United States Patent [19]

Shriner et al.

[11] Patent Number: 5,685,192
[45] Date of Patent: Nov. 11, 1997

[54] APPARATUS FOR DETERMINING THE MOISTURE CONTENT OF SOLIDS OVER A RANGE OF RELATIVE HUMIDITIES AND TEMPERATURES

[75] Inventors: Katherine A. Shriner, Rochester; Robert A. Curtis, Webster; Thomas F. Falls, Hilton, all of N.Y.

[73] Assignee: Eastman Kodak Company, Rochester, N.Y.

[21] Appl. No.: 629,856

[22] Filed: Apr. 9, 1996

[51] Int. Cl.$^6$ .................................................. G01N 50/04
[52] U.S. Cl. ............................ 73/73; 73/74; 73/865.6
[58] Field of Search .......................... 73/73, 74, 76, 73/865.6; 177/25.13, 25.14; 364/556

[56] References Cited

U.S. PATENT DOCUMENTS

| | | | |
|---|---|---|---|
| 3,254,421 | 6/1966 | Kielsmeir et al. | 73/73 |
| 3,469,455 | 9/1969 | Iwata | 73/865.6 |
| 4,750,143 | 6/1988 | Heitz et al. | 73/76 |
| 4,838,705 | 6/1989 | Byers, Jr. et al. | 177/25.14 |
| 4,889,201 | 12/1989 | Oldendorf et al. | 177/25.14 |
| 5,211,252 | 5/1993 | Henderson et al. | 177/25 |
| 5,249,456 | 10/1993 | Gilmore et al. | 73/73 |
| 5,251,476 | 10/1993 | Gilmore et al. | 73/73 |
| 5,257,532 | 11/1993 | Hayakawa et al. | 364/556 |
| 5,285,672 | 2/1994 | Yao | 73/865.6 |
| 5,499,532 | 3/1996 | Kaiho et al. | 73/76 |

FOREIGN PATENT DOCUMENTS

| | | | |
|---|---|---|---|
| 2699280 | 6/1994 | France | 73/73 |
| 604863 | 7/1948 | United Kingdom | 73/73 |

*Primary Examiner*—Ronald L. Biegel
*Attorney, Agent, or Firm*—James D. Leimbach

[57] ABSTRACT

A method and apparatus for measuring isotherms comprising a two-pressure and/or two-temperature humidity generator having a temperature controlled internal chamber and a microbalance mounted externally such that the mass of a sample suspended within the chamber can be determined without disturbing the controlled environment surrounding the sample. The two-pressure humidity generator has a front panel for controlling humidity and temperature within the internal chamber and an access port that extends into the internal chamber. The balance is situated near the port such that the balance mechanism extends within the internal cheer. The balance mechanism utilizes a means for holding a sample within the chamber such that the mass of the sample can be determined as it equilibrates to the temperature and relative humidity maintained within the internal cavity.

20 Claims, 2 Drawing Sheets

APPARATUS FOR DETERMINING THE MOISTURE CONTENT OF SOLIDS OVER A RANGE OF RELATIVE HUMIDITIES AND TEMPERATURES

FIELD OF INVENTION

The invention relates generally to the field of generating and measuring moisture isotherms, and in particular to generation and measurement of isotherms without removal of a sample from a controlled environment.

BACKGROUND OF THE INVENTION

For products whose performance changes as a function of storage time, manufacturers frequently determine the mechanism of change. Product degradation may result from reaction with oxygen or oxidants, from hydrolysis reactions involving water, from physical transport of chemicals within a product, or from other mechanisms. When mechanisms involving water are suspected, a useful tool is to determine the product's moisture content over a range of relative humidities (RH) since storage at higher RH values increases the moisture content (MC) of humidity sensitive products. In some cases, products have been reformulated with humectants or drying agents to control their moisture content. Plots of moisture content versus RH, referred to as moisture isotherms or Langmuir sorption isotherms, allow comparison of moisture uptake for various products. The invention described below involves a new method for determining the moisture sorption isotherm and can be applied to a wide range of products.

There are a variety of existing methods and devices to measure an isotherm. All of these require two separate pieces of equipment: a device to control the storage RH and temperature; and a device to determine moisture at the storage conditions. Existing methods for controlling the storage RH include use of environmental chambers and use of saturated salt solutions. However, problems exist with each of these methods. Environmental chambers are typically either walk-in units or stand-alone units. Such units may suffer from variations in RH and/or temperature as a function of position inside the chamber. The conditions within the chamber can show a wide degree of variation from good to extremely poor depending on the quality of air flow. Saturated salt solutions require impeccable laboratory technique to achieve accurate and precise control over sample RH. A weak point in measuring isotherms is often the control of the temperature and RH around a sample. To address this problem, the present invention proposes an alternative technique for controlling sample storage conditions.

The techniques to determine moisture in a sample are extremely varied. They include spectroscopic techniques, chromatography, Karl-Fischer titration's, and gravimetric techniques. Results from these techniques correlate with each other, but the absolute moisture content may be different depending on the method. Gravimetric techniques are probably the most popular because mass change is directly traceable to moisture change. However, there are a number of problems associated with gravimetric techniques including difficulty in measuring small mass differences and noise in the measurement due to the balance. Instrument noise can be related to temperature and RH changes in the air around a balance, electronic drift, or building vibrations. Strictly controlling the temperature and RH around the balance and isolating it from vibration can reduce some of the noise. Additionally, fluctuation in temperature or RH around the sample will cause uncertainty in the measurement of the sample's moisture content. More will be said about RH-induced problems later.

Moisture content (MC) is defined as the mass of moisture in a product normalized for the sample size. In gravimetric measurements, the mass of moisture is measured by determining the mass of the sample at a storage RH ($M_{wet}$) and the mass of the dried sample ($M_{dry}$). The amount of moisture in the sample is the difference between these two values: $M_{wet}-M_{dry}$. Normalizing the amount of moisture by the sample size can be done by dividing the amount of moisture by either $M_{wet}$ or $M_{dry}$. Moisture contents are also typically presented as a percentage of the mass that is water. To calculate moisture content-dry basis, Equation 1 is used:

$$MC(\text{dry basis})=100\times(M_{wet}-M_{dry})/M_{dry} \quad \text{Equation 1:}$$

Moisture content can also be calculated on a wet basis as by using Equation 2.

$$MC(\text{wet basis})=100\times(M_{wet}-M_{dry})/M_{wet} \quad \text{Equation 2:}$$

The wet mass is determined by putting a sample in a temperature controlled RH environment and weighing the sample when it reaches equilibrium with the surrounding environment. If this mass is determined by placing a balance in the controlled environment, then the mass may be in error since balances change readings as a function of RH. If the sample is removed from the controlled environment to be weighed, then the sample will start to equilibrate to the RH condition of the weighing area. The mass determination becomes difficult to analyze since the values will change with time. Therefore, making mass measurements without removing the sample from the controlled environment would be preferred.

The moisture sorption isotherm is made by measuring the moisture content of a product at a number of different RH values. Therefore, mass data is required for many different RH conditions. This fact means that either a large number of RH controlled devices are required or that a few devices be used but the RH changed after each reading. Since the environmental chambers used for this test are expensive, changing RH after each reading is usually necessary. It should be noted, however, that requiring an operator to change the RH of the test chamber after each equilibrium reading can be extremely labor intensive.

Even when taking precautions for many factors, the moisture content measurement is usually somewhat irreproducible. Most of the noise in the measurement comes from control of temperature and RH around the sample.

As can be seen by the foregoing discussion, there remains a need within the art for a method and apparatus that can sequentially test a sample under numerous precisely controlled environments without the necessity of removal of the sample from the test equipment. These and other shortcomings within the prior art are addressed by the present invention.

SUMMARY OF THE INVENTION

The present invention is directed to overcoming one or more of the problems set forth above. Briefly summarized, one aspect of the present invention includes an apparatus for measuring isotherms comprising: a humidity generator having an internal cavity; a means for controlling humidity and temperature within the internal cavity; a port that extends into the internal cavity; a balance mechanism situated near the port such that the balance mechanism extends within the internal cavity; a holding means such that the balance mechanism holds a sample within the cavity; and a means for determining the mass of the sample within the cavity. An apparatus comprising a two-pressure humidity generator combined with a microbalance mounted above the humidity generator's internal cavity with the two being interfaced by a general purpose computer would be such an apparatus.

The above and other objects of the present invention will become more apparent when taken in conjunction with the following description and drawings wherein identical reference numerals have been used, where possible, to designate identical elements that are common to the figures.

ADVANTAGEOUS EFFECT OF THE INVENTION

The present invention has the following advantages: (1) it allows a determination of mass data without having to remove a sample from the controlled environment; (2) it permits for the changing of a controlled environment without moving the sample; (3) it creates a system that can be controlled by an external computer which in turn allows for the sequencing of controlled environments and the determination of equilibrium points; (4) it produces more accurate results than those obtained by the prior art; (5) it allows for testing of a sample at different temperatures; (6) it allows for more accurate control of RH and temperature around the sample during mass determination; and (7) it allows for determination of a moisture sorption isotherm on a single sample.

DETAILED DESCRIPTION OF THE INVENTION

Figure 1:
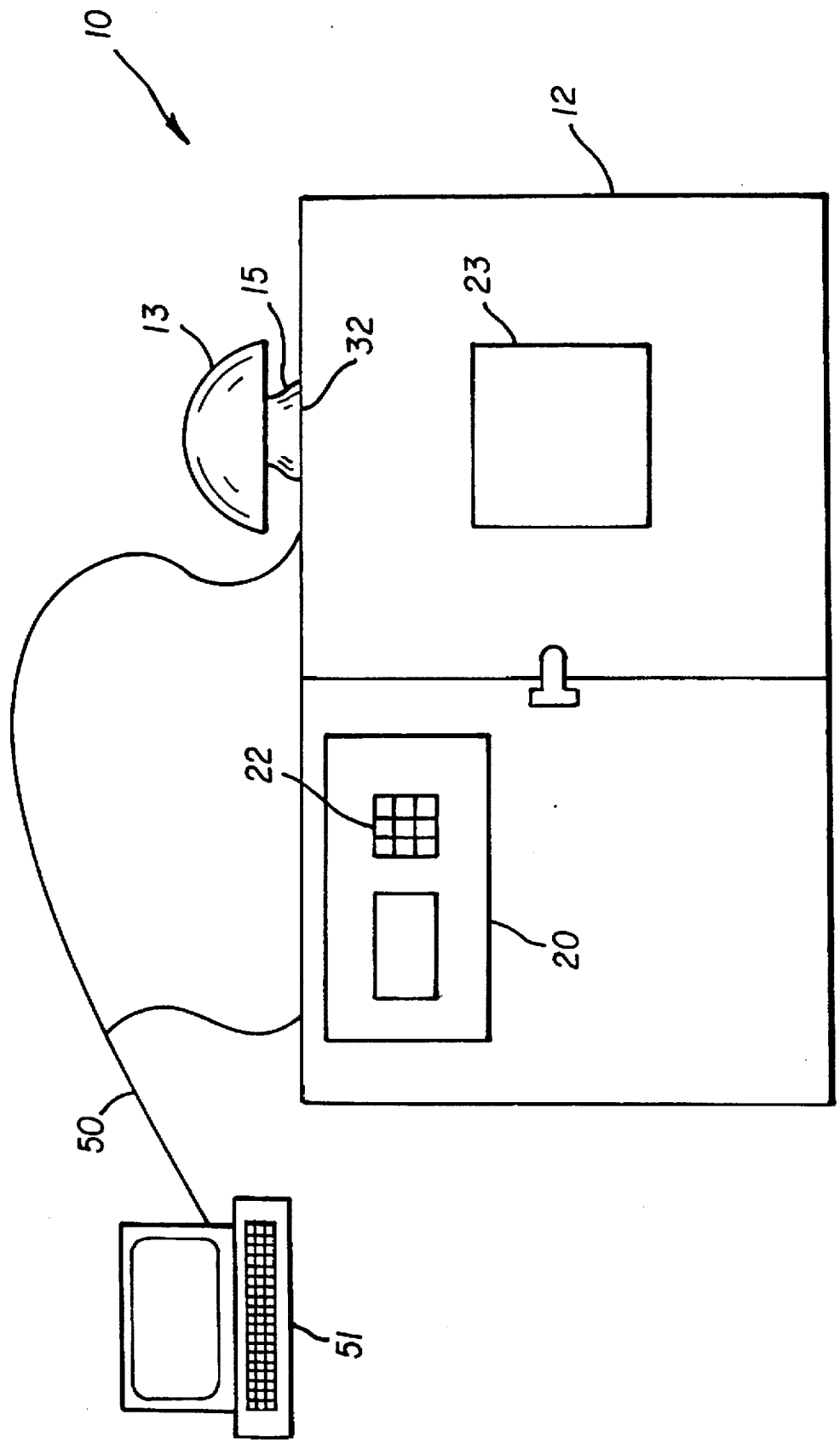
FIG. 1 is a front view of the present invention.

We have developed a technique for obtaining moisture isotherms of test samples to a high degree of accuracy and precision. Referring to FIG. 1, the device 10 used to practice this technique employs a sensitive recording microbalance 14 suspended above an environmental chamber 23 which is precisely controlled by a two-pressure humidity generator 12. The sample, hanging within the environmental chamber 23 is connected to the microbalance 14 via a hangdown wire 42 which passes through an access port 32 in the environmental chamber 23. The humidity generator 12 produces a precisely controlled relative humidity which is supplied to the temperature controlled test chamber 23. The mass of the sample hanging within this controlled environment can thus be continuously measured via the recording microbalance 14.

As previously discussed, there are problems in the existing methods, and the associated apparatus, that control storage RH via environmental chambers or saturated salt solutions. The present invention solves the problems associated with controlling the sample storage conditions by using a two-pressure humidity generator 12 to supply known RH air to a precisely temperature controlled test chamber. This device has previously been used to calibrate RH sensors and is noted for accurate and tight control over RH and temperature. The two-pressure generator 12 acts by first saturating air to 100% RH at a given temperature and elevated pressure. When this air is isothermally expanded to ambient pressure inside a temperature controlled chamber 23, the RH at the test chamber pressure will depend on the initial saturation pressure. RH is determined as shown in equation 3:

$$RH \approx 100 \times (P_{chamber}/P_{saturator})  \quad \text{Equation 3:}$$

where %RH is the percent relative humidity, $P_{chamber}$ is the air pressure in the chamber, and $P_{saturator}$ is the pressure in the saturator. It is necessary to apply corrections to this equation to compensate for such things as the non-ideal behavior of air, over or under saturation of the air due to non-isothermal conditions, etc.

Currently, there are very few two-pressure generators in existence. The preferred embodiment of the present invention employs a Thunder Scientific Benchtop Two-Pressure Humidity Generator 12, Series 2500 that has been modified to allow for incorporation and proper positioning of a sample. The Thunder Scientific humidity generator 12 is designed to be a bench-top unit. Typically, the humidity generators from Thunder Scientific have a side port. The present invention is created with a top port 32 which is utilized for making mass determinations on a sample. The existence of the top port 32 allows the microbalance to be positioned above the internal cavity 23 of the humidity generator 12 so that the hangdown wire 42 from the balance passes through the top access port 32 and into the internal cavity 23. This in turn allows for measurement of the sample mass within the confines of the internal cavity.

The Thunder Scientific 2500 is based on the NIST developed two-pressure method of producing known atmospheres of relative humidity through application of Dalton's law of partial pressures which states that the pressure exerted by a mixture of gases in a given volume is equal to the sum of the pressures which would be exerted by each individual gas if it alone occupied the same volume at the same temperature. The principle of the two-pressure method of producing known atmospheres assumes that water vapor pressure remains a fraction of the total pressure under Dalton's law. Under the two pressure method, as employed by the present invention, air is first saturated to 100% humidity at some temperature and back calculated pressure. The 100% RH air is then isothermally expanded to obtain the desired relative humidity at the pressure and temperature of the chamber.

The Thunder Scientific 2500 has an on-board computer and control system (not shown) to perform calculations and control functions. The on-board computer system monitors and controls the temperature and humidity within the cavity 23 and the operation of the humidity generator 12 itself. The settings may be controlled either through the internal keyboard 22 on front panel 20 or through an external computer 51. External equipment may be interfaced via an RS-232 interface. The on-board computer has no capability to control past or future setpoints. The control capability of sequential setpoints can be accomplished through an external computer via the RS-232 interface port. Therefore, the preferred embodiment of the present invention employs an external computer 51 to sequence temperature and RH conditions within the chamber via an RS-232 interface. The essential ingredients of the present invention are operable without the external computer via the keyboard entry panel to the Thunder Scientific 2500.

While the preferred embodiment employs a Thunder scientific 2500, other devices for generating precisely controlled, variable, RH and temperature environments could be used. They may include two-temperature generators, two-pressure generators, and two-temperature/two-pressure generators. Environmental chambers which control the environment via a steam generator could also be employed. The preferred embodiment employs Two-Pressure Thunder Scientific humidity generator to achieve precise RH control over a wide range of humidities and temperatures.

Figure 2:
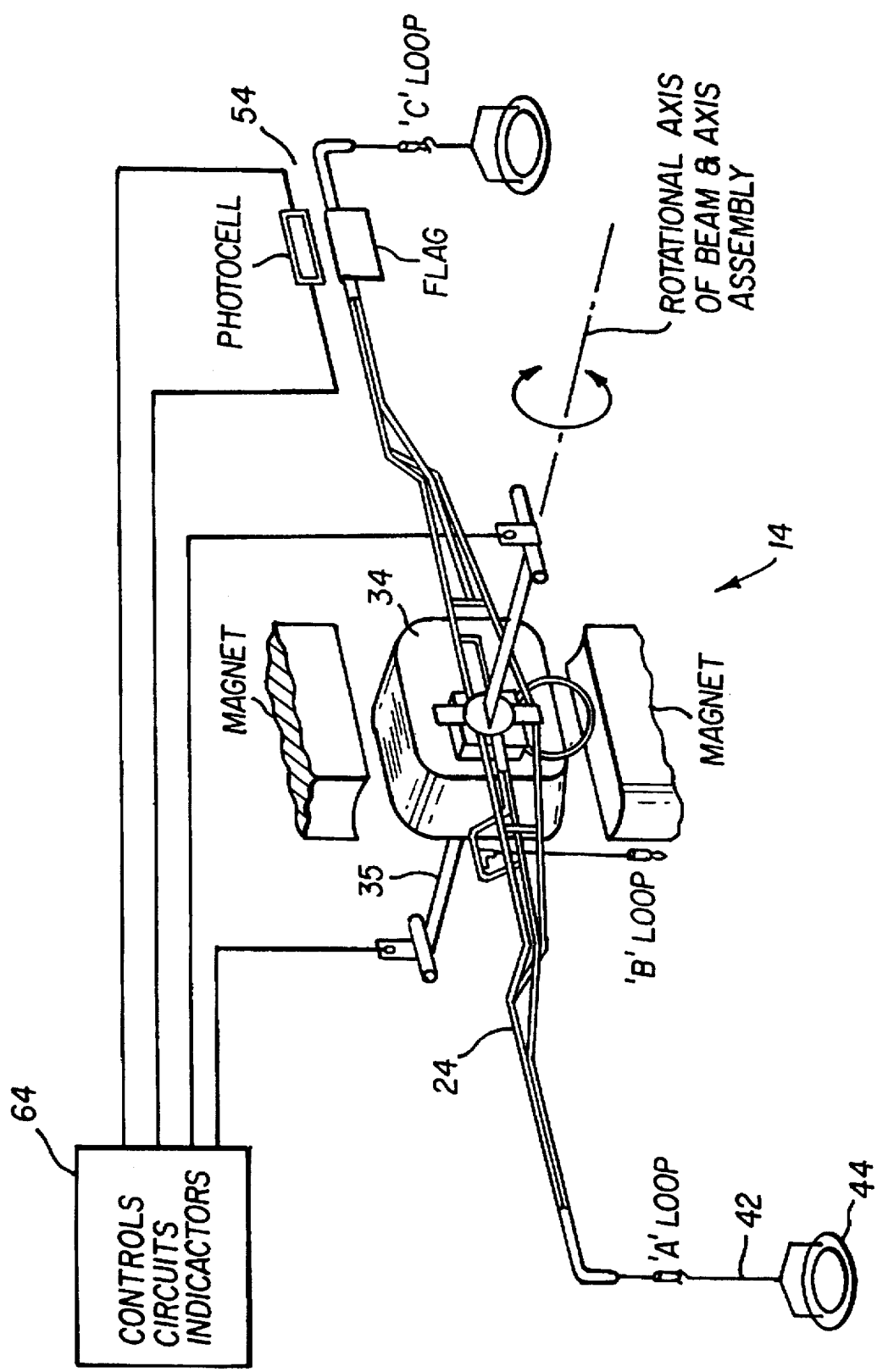
FIG. 2 is a perspective view of the microbalance used by the present invention.

Referring now to FIG. 2, an exploded view of the microbalance as used by the preferred embodiment of the invention can be seen. The microbalance 14 used by the preferred embodiment of the present invention is a Cahn D-200 recording microbalance, which can accommodate masses up to 3 ½ grams and as small as 0.1 micrograms. The microbalance 14 is contained within dome 13. The unit is positioned above the cavity 23, and is isolated from external building vibration. A flexible material 15 is used to connect the balance/dome unit 13 to the internal cavity 23 such that the environment inside the test chamber is preserved and the microbalance does not see any vibration from the humidity generator 12. The microbalance 14 is divided into two sections. One section is a control unit 64 comprised of electronics and the other section is a Weighing Unit which detects the actual mass of a sample. The Cahn-D200 microbalance is also capable of measurements under high vacuum which is useful for determining the dry mass of the sample. The balance mechanism operates as a force-to-current converter. The unit consists of: 1) a balance beam 24 pivoting about the center of a taut ribbon; 2) a torque motor coil 34 located in a permanent magnetic field and also mounted to the taut ribbon 35; 3) sample suspension fixtures 44; 4) a beam position sensor system 54; and 5) control, circuitry and indicators 64. The microbalance 14 operates by having the torque motor 34 keep the balance beam in a reference position. This is accomplished by generating currents in the torque motor coil 34 in response to weight being placed on the sample suspension fixture 44 on the balance beam 24. The more force placed on the sample suspension fixtures 44 the more force is required by the torque motor coil 34 to keep the balance beam 24 in place.

Other microbalances, such as a Cahn C-2000 with a strip chart readout (not shown), or other microbalances that give a digital readout could conceivably be substituted for the Cahn D-200. Where the D-200 requires a manufacturer specified personal computer, other microbalances may not. These microbalances still result in a visually discernible output which can be correlated by an operator to the relative humidity within the humidity generators internal cavity.

To measure the MC of a material using the preferred Cahn D-200 microbalance, a sample is hung from the sample suspension fixture 44 which is attached to one end of a wire like balance beam 24. The sample suspension fixture is long enough to pass down through the top access port 32 and into the temperature controlled test chamber 23 of the two-pressure generator 12. Controlled temperature and RH air is flowed over the sample. The balance beam 24 is attached to a sensitive recording balance as previously described. The temperature around the balance is strictly controlled and the balance itself is isolated from vibration. This setup allows for accurate measurement of the sample's mass as it equilibrates to the set RH and temperature. Following equilibration of the sample, the RH is changed (raised or lowered) and mass data accumulated at the new RH value. Therefore a moisture isotherm can be generated on a single sample and the equilibrium mass data obtained without having to remove the sample from the temperature and RH controlled environment.

To determine moisture content, the sample's wet weight and dry weight must be determined. Moisture content (MC), dry basis, is defined by the Equation 1 where $M_{wet}$ is the mass of the sample at the storage RH; and $M_{dry}$ is the mass of the sample with all of the water removed or at 0% RH.

Dry weight can be determined by drying samples using microwave or infrared treatment, heating in an oven, flowing a dry gas such as nitrogen over the sample, evacuation of a sample, or a combination of these techniques such as heating while evacuating. As the Cahn microbalances are capable of operation under vacuum and low to medium vacuums have been shown to be non-detrimental to our test samples, determination of the dry mass via evacuation under controlled temperatures is the preferred method of this invention.

The wet weight is determined by putting a sample in a temperature controlled RH environment and weighing the sample when it reaches equilibrium with the surrounding environment. Previous experiments have shown that problems exist in weighing a sample after it has been removed from a first controlled RH condition and placed in a second controlled RH condition because the sample begins to equilibrate to the second RH condition immediately being placed in the second controlled condition. Therefore, making the measurement of the mass of the sample without removing the sample from the controlled environment is preferred. The present invention allows for the measurement of a sample's mass at equilibrium without removing it from the controlled environment. Furthermore, a complete isotherm can be generated on a single sample by alternating the environment around the sample without removing it from the test chamber.

Generation of a complete isotherm requires mass data at many RH values. This fact means that either a large number of RH controlled devices are required or that a few devices be used but the RH changed after each reading. Since the environmental chambers used for this test are expensive, changing RH after each reading is necessary. Requiring an operator to change the RH after each reading can be extremely labor intensive. By interfacing the microbalance and the two-pressure humidity generator via an external computer, the RH can be altered and the resulting equilibrium mass of the sample determined for numerous choices of controlled environments. The computer sets the RH value, records mass data as a function of time, determines when the sample is equilibrated, and ramps the generator to the next RH.

The preferred embodiment of the interface program allows the operator to specify 1) test parameters including RH, temperature, and flow rate inside the internal cavity, 2) number of conditions per run, 3) the data logging interval, 4) the minimum time that the humidity generator must maintain each specified environmental condition, 5) the equilibrium criteria, as defined by a mass change per time, that must be met, once the minimum time criteria has been satisfied, before the computer can sample the humidity generator to the next specified environmental condition, and 6) the maximum time the humidity generator is to maintain the environmental condition even if the equilibrium criteria is not satisfied. The interface program also creates data files if 1) mass of the sample and humidity generator conditions and system information versus time, as specified by the data logging interval and 2) equilibrium values of mass and humidity generator variables as defined at the time directly before the generator is sampled to the next specified environmental condition.

Therefore, use of an external computer to interface the system allows a complete isotherm to be generated on a single sample without the need for extensive operator intervention, and as such is a preferred embodiment of the invention.

Even when taking precautions for many factors, the moisture content measurement is usually somewhat irreproducible. Most of the noise in the measurement comes from control of temperature and RH around the sample. The configuration of the present invention alleviates many of the problems that existed in the prior art.

The present invention, while being created to measure isotherms of photographic film samples, is useful for a number of other industries, including food, pharmaceuticals, agriculture, and consumer products. Photographic film and film constituents fall within this group of industries.

The invention has been described with reference to a preferred embodiment. However, it will be appreciated that variations and modifications can be effected by a person of ordinary skill in the art without departing from the scope of the invention.

PARTS LIST

10 Device
12 humidity generator; two-pressure and/or two-temperature
13 dome
14 microbalance
15 flexible material
20 front panel
22 keyboard
23 cavity
24 balance beam
32 access port
34 torque motor coil
35 torque ribbon
42 hangdown wire
44 sample suspension fixture
50 RS-232 interface
51 external computer
54 beam position sensor
64 control circuitry and indicators

We claim:

1. A device for measuring isotherms comprising:
   a humidity generator having an internal cavity;
   means for changing and controlling humidity and temperature within the internal cavity to establish a sequence of environments each potentially having a different humidity and a different temperature for each environment;
   a port that extends into the internal cavity;
   a balance, having a balance mechanism with means for holding a sample, situated near the port such that the balance mechanism extends within the internal cavity;
   means for determining the mass of a sample within the internal cavity via the balance mechanism for each environment; and
   means for determining a final mass for each environment where a calculated change in the mass of the sample effectively drops below a redetermined value;
   means for displaying humidity and temperature within the cavity, and the final mass in a visually discernible manner; and
   means for sequencing through the sequence of environments.

2. The invention of claim 1 wherein the port is located in the top of the humidity generator's internal cavity.

3. The invention of claim 1 wherein the balance further comprises a microbalance.

4. The invention of claim 1 wherein the humidity generator further comprises any one of the following: a two-pressure humidity generator; a two-temperature humidity generator; or a two-pressure/two-temperature humidity generator.

5. The invention of claim 1 wherein the means for determining the mass of the sample further comprises means for continuously monitoring the mass of the sample.

6. The invention of claim 1 wherein the humidity generator further comprises a relative humidity generator that allows selection of humidity of a predetermined amount.

7. The invention of claim 1 further comprising means for determining when the sample has reached equilibrium within the controlled environment.

8. The invention of claim 1 further comprising means for maintaining the test chamber at a constant temperature and RH until the sample reaches equilibrium with the environment.

9. The invention of claim 8 further comprising means for adjusting the environment within the test chamber and for determining the mass of the sample continuously until equilibrium is again reached.

10. A method of generating isotherms for a given sample comprising the steps of:
    providing a humidity generator having an internal cavity with a port that extends into the internal cavity;
    providing a balance, with means for holding a sample, situated near the port such that the balance mechanism extends within the internal cavity;
    attaching the sample to the balance mechanism so that the sample is held within the internal cavity;
    adjusting the temperature and humidity within the internal cavity to set a predetermined environment;
    repeatedly measuring the mass of the sample on the balance mechanism;
    determining when the mass of the sample has ceased changing within a predetermined amount;
    generating parameters of humidity and temperature within the cavity and the final mass of the sample;
    sequencing the foregoing steps through a plurality of environments.

11. The method of claim 10 further comprising the step of developing a moisture sorption isotherm.

12. The method of claim 10 wherein the step of providing a humidity generator further comprises providing one of the following: either a two-temperature humidity generator, a two-pressure humidity generator, or a two-pressure/two-temperature humidity generator.

13. The method of claim 10 further comprising the step of continuously monitoring the mass of the sample.

14. The method of claim 13 further comprising the step of generating a relative humidity of a predetermined amount.

15. The method of claim 13 further comprising the step of maintaining the generator environment at a constant until the sample reaches a predetermined equilibrium.

16. The method of claim 10 further comprising the step of waiting for the sample to come into equilibrium.

17. The method of claim 16 further comprising the step of determining the mass of the sample.

18. An apparatus for measuring isotherms comprising:
    a humidity generator having an internal cavity, the humidity generator being either a two-pressure, two-temperature, or two-pressure/two-temperature humidity generator;
    means for adjusting humidity and temperature within the internal cavity;
    a port that extends into the internal cavity;

a balance situated near the port such that the balance mechanism extends within the internal cavity;

holding means such that the balance mechanism holds a sample within the cavity;

means for determining the mass of the sample on the balance mechanism while the sample remains within the cavity and for determining when a final mass is reached wherein changes in the mass fall below a predetermined amount; and means for placing the humidity generator through a sequence of environments.

19. The invention of claim 18 further comprising means for maintaining the internal cavity at a constant temperature and relative humidity until the sample's mass reaches equilibrium.

20. The invention of claim 18 further comprising means for ramping the environment within the generator to a new condition and for measuring the mass of the sample until equilibrium is again reached.

* * * * *

UNITED STATES PATENT AND TRADEMARK OFFICE
CERTIFICATE OF CORRECTION

PATENT NO. : 5,685,192
DATED : November 11, 1997
INVENTOR(S) : Katherine A. Shriner, et al It is certified that error appears in the above-identified patent and that said Letters Patent is hereby corrected as shown below:

Cover Page      Insert --Related U.S. Application Data, [60] Provisional 60,003,310, filed September 6, 1995--

Signed and Sealed this

Nineteenth Day of May, 1998

*Attest:*

BRUCE LEHMAN

*Attesting Officer*      *Commissioner of Patents and Trademarks*